(12) United States Patent
Kankan et al.

(10) Patent No.: US 8,242,269 B2
(45) Date of Patent: Aug. 14, 2012

(54) PROCESSES FOR THE PREPARATION OF PALIPERIDONE AND PHARMACEUTICALLY ACCEPTABLE SALTS THEREOF AND INTERMEDIATES FOR USE IN THE PROCESSES

(75) Inventors: Rajendra Narayanrao Kankan, Maharashtra (IN); Dharmaraj Ramachandra Rao, Maharashtra (IN); Srinivas Laxminarayan Pathi, Karnataka (IN)

(73) Assignee: CIPLA Limited, Mumbai (IN)

( * ) Notice: Subject to any disclaimer, the term of this patent is extended or adjusted under 35 U.S.C. 154(b) by 191 days.

(21) Appl. No.: 12/681,767

(22) PCT Filed: Oct. 9, 2008

(86) PCT No.: PCT/GB2008/003408
§ 371 (c)(1),
(2), (4) Date: Jul. 12, 2010

(87) PCT Pub. No.: WO2009/047499
PCT Pub. Date: Apr. 16, 2009

(65) Prior Publication Data
US 2010/0298565 A1    Nov. 25, 2010

(30) Foreign Application Priority Data
Oct. 9, 2007    (IN) .......................... 2013/MUM/2007

(51) Int. Cl.
*C07D 239/70*    (2006.01)
(52) U.S. Cl. ..................................................... 544/282
(58) Field of Classification Search ................... 544/282
See application file for complete search history.

(56) References Cited

U.S. PATENT DOCUMENTS
5,158,952 A   10/1992   Janssen et al.

FOREIGN PATENT DOCUMENTS
| | | |
|---|---|---|
| CN | 101245065 A | 8/2008 |
| EP | 0368388 A2 | 5/1990 |
| WO | 2008024415 A2 | 2/2008 |
| WO | 2008144073 A1 | 11/2008 |
| WO | 2009010988 A1 | 1/2009 |
| WO | 2009015828 A1 | 2/2009 |
| WO | 2009047499 A2 | 4/2009 |
| WO | 2009047499 A3 | 4/2009 |

OTHER PUBLICATIONS

Foreign communication from the priority application—International Preliminary Report on Patentability, PCT/GB2008/003408, Apr. 13, 2010, 9 pages.

Foreign communication from the priority application—International Search Report and Written Opinion, PCT/GB2008/003408, Apr. 17, 2009, 15 pages.

*Primary Examiner* — James O Wilson
*Assistant Examiner* — Brian McDowell
(74) *Attorney, Agent, or Firm* — Conley Rose, P.C.; Rodney B. Carroll

(57) ABSTRACT

The present invention relates to novel compounds of formula (VIII) and (X), processes for their preparation and their use in the preparation of paliperidone or a salt thereof. There is also provided by the present invention novel processes for preparing intermediates for use in the preparation of paliperidone or a salt thereof, and novel processes for preparing paliperidone or a salt thereof.

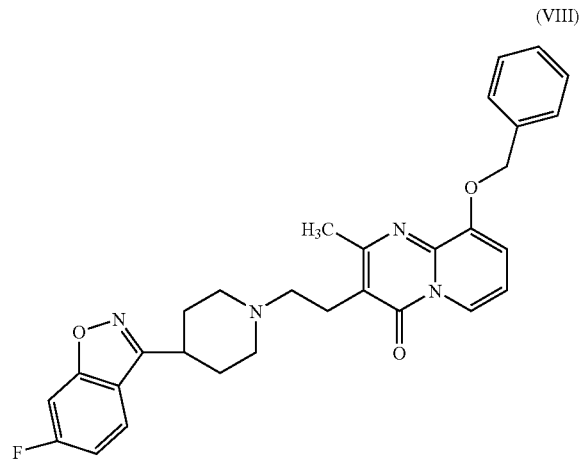

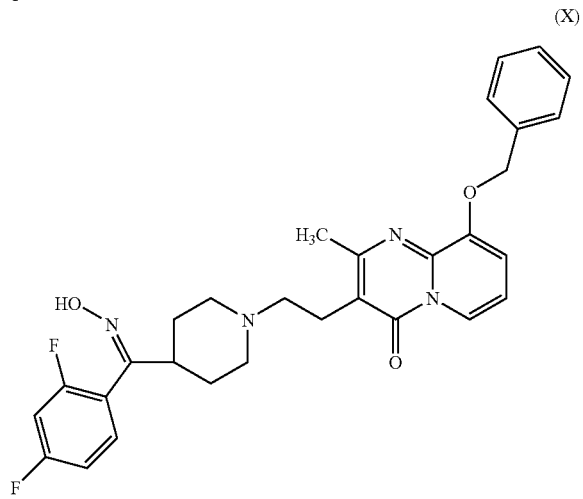

10 Claims, No Drawings

PROCESSES FOR THE PREPARATION OF PALIPERIDONE AND PHARMACEUTICALLY ACCEPTABLE SALTS THEREOF AND INTERMEDIATES FOR USE IN THE PROCESSES

CROSS-REFERENCE TO RELATED APPLICATIONS

This application is a filing under 35 U.S.C. 371 of International Application No. PCT/GB2008/003408 filed Oct. 9, 2008, entitled "Processes for the Preparation of Paliperidone and Pharmaceutically Acceptable Salts Thereof and Intermediates for Use in the Processes," claiming priority of Indian Patent Application No. 2013/MUM/2007 filed on Oct. 9, 2007, which applications are incorporated by reference herein in their entirety.

FIELD OF THE INVENTION

The present invention relates to processes for the preparation of paliperidone or its pharmaceutically acceptable salt, and processes for preparing intermediates useful in the synthesis of paliperidone, or its pharmaceutically acceptable salts.

BACKGROUND OF THE INVENTION

Schizophrenia is a common and disabling psychotic disorder characterized by extreme disturbances of cognition and thought, affecting language, perception and sense of self. Despite the availability of a number of agents for the treatment of schizophrenia, it remains a significant burden on healthcare systems. Most of the antipsychotic drugs, although effective against psychosis, do not improve and may even exacerbate the negative symptoms of schizophrenia.

Paliperidone, an atypical antipsychotic, is an active metabolite of risperidone used for the treatment of schizophrenia and bipolar disorder. While its specific mechanism of action is unknown, it is believed that paliperidone and risperidone act via similar, if not the same, pathways.

Paliperidone, i.e, 9-hydroxyrisperidone, is chemically known as 3-[2-[4-(6-fluoro-1,2-benzisoxazol-3-yl)-1-piperidinyl]ethyl]-6,7,8,9-tetrahydro-9-hydroxy-2-methyl-4H-pyrido[1,2-a]pyrimidin-4-one and has the following structural formula (I).

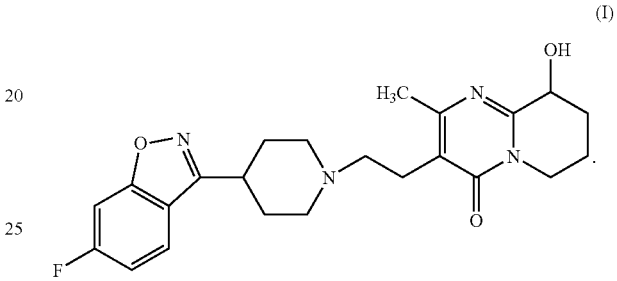

U.S. Pat. No. 5,158,952 and its equivalent EP 368,388 disclose paliperidone, compositions comprising paliperidone and methods of its use. The synthetic process employed is depicted in the following scheme.

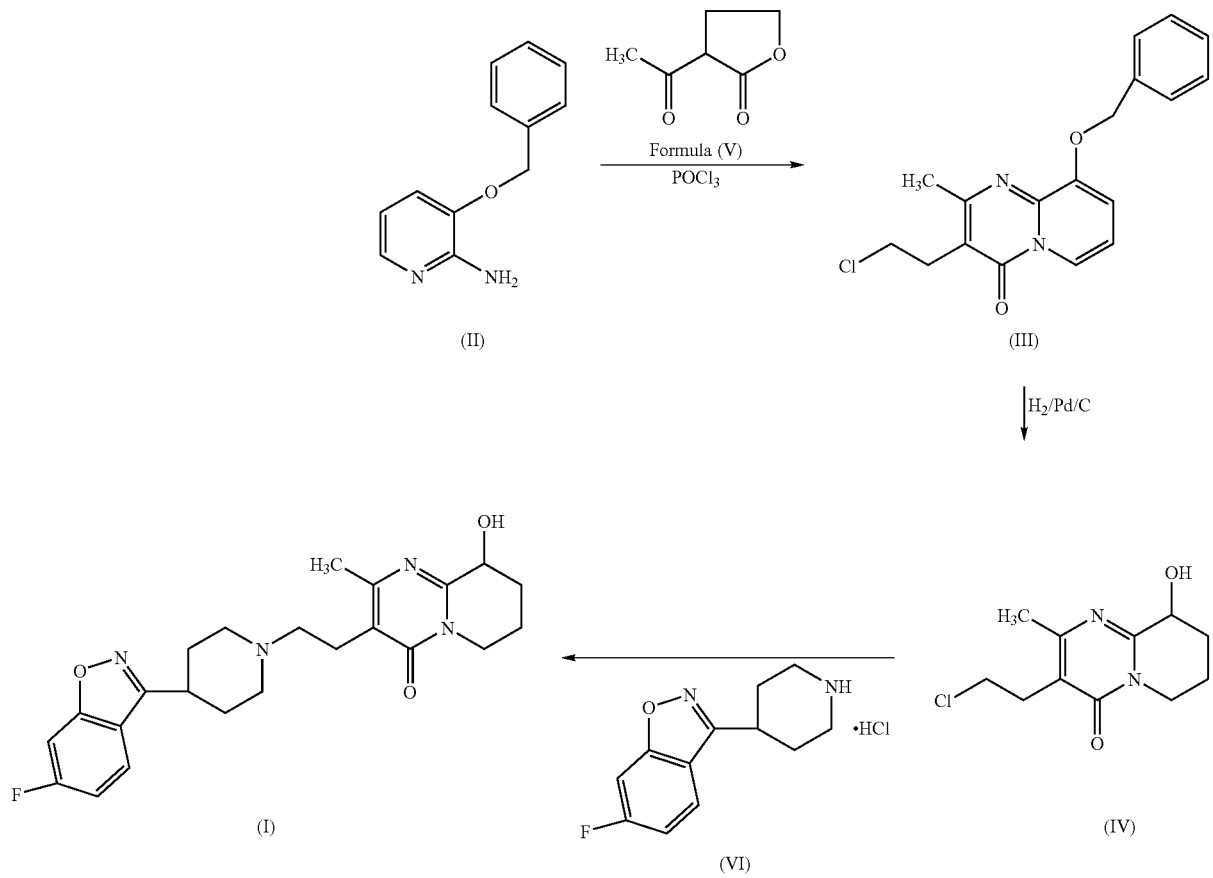

wherein the compound of formula (II) is reacted with the compound of formula (V) at 90° C. for 5 hours to yield the compound of formula (III) which is purified by column chromatography using trichloromethane and methanol and further recrystallized from isopropanol. The compound of formula (III) is further reduced to the compound of formula (IV) in methanol using a palladium on carbon as catalyst, which is further condensed with the compound of formula (VI) to yield paliperidone of formula (I).

The process disclosed in the U.S. Pat. No. 5,158,952 has several disadvantages. First, the intermediate (III) is obtained as an oily mass. This oily mass contains impurities which are difficult to separate by crystallization. In this process, a solid product is obtained only after purification by column chromatography thereby making the process non economical on an industrial scale. Second, hydrogenolysis of the compound of formula (III) to the compound of formula (IV) leads to undesirable dechlorination resulting in the des-chloro impurity of compound of formula (VII).

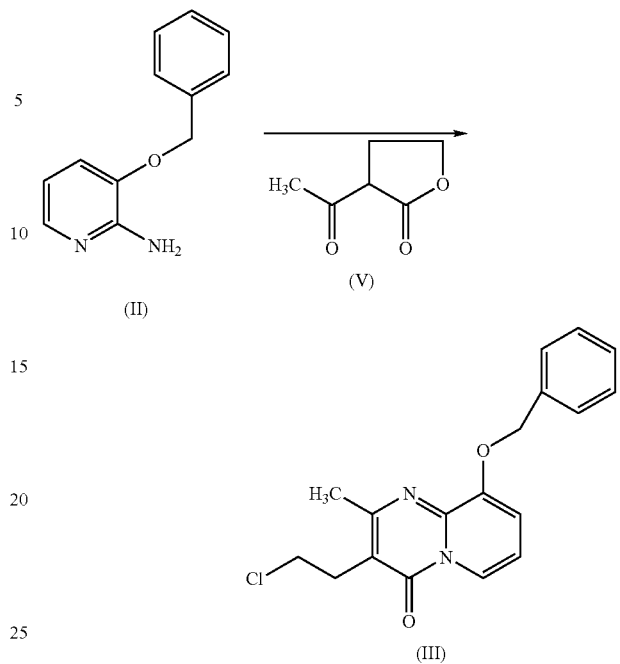

(II)

(V)

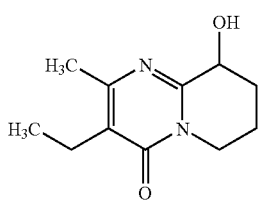

(VII)

Paliperidone thus obtained by condensation of the compound of formula (IV) with the compound of formula (VI) is of poor quality and is further purified by column chromatography and solvent crystallizations, thereby making the process time consuming and expensive.

Therefore, there exists a need for a more economical and efficient method of making pure paliperidone which is suitable for industrial scale up.

Objects of the Invention

It is an object of the present invention to provide novel intermediates for the synthesis of paliperidone or its pharmaceutically acceptable salts.

It is another object of the present invention to provide processes for the preparation of novel intermediates used in the synthesis of paliperidone or its pharmaceutically acceptable salts.

It is yet another object of this invention to provide novel processes for the preparation of paliperidone or its pharmaceutically acceptable salts using novel intermediates.

SUMMARY OF THE INVENTION

According to a first aspect of the present invention, there is provided a process for preparing a compound of formula (III) comprising condensing a 3-benzyloxy-2-aminopyridine (II) with an α-acyl lactone (V).

(III)

Advantageously, the condensation is carried out in the presence of a dipolar aprotic solvent. Preferably, the dipolar aprotic solvent is present in a catalytic amount. Preferably, the condensation is carried out in the presence of an activating agent. Most preferably, the condensation is carried out in the presence of an activating agent and a catalytic amount of a dipolar aprotic solvent.

In an embodiment, the dipolar aprotic solvent is selected from the group consisting of N,N-dimethylformamide (DMF), N,N-dimethylacetamide (DMA), dimethylsulfoxide (DMSO), 1-methyl-2-pyrrolidinone, pyridine and acetic anhydride. Preferably, the dipolar aprotic solvent is DMF.

In an embodiment, the activating agent is a halogenating reagent, typically a chlorinating agent suitably selected from the group consisting of thionyl chloride, phosphorous oxychloride, phosphorous trichloride, phosphorous pentachloride, oxalyl chloride and phosgene. Preferably, the activating agent is phosphorous oxychloride. Alternatively, other halogenating agents may be used, for example, brominating agents. In this case, the chloro moiety in compound (III) above would be replaced with a bromo moiety, i.e., a compound of formula (IIIa).

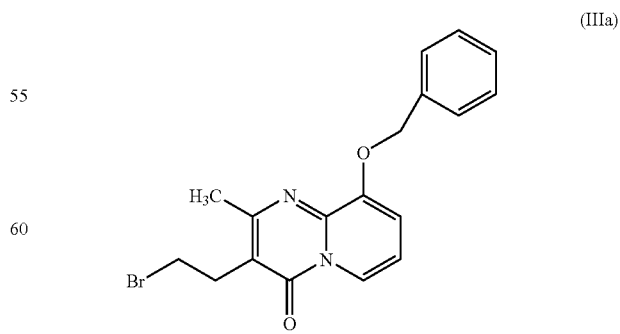

(IIIa)

In another alternative, the reaction conditions of the condensation of compound (II) with compound (V) would be such that a different leaving group were present in place of the chloro moiety on compound (III), i.e., the compound of formula (IIIb) below wherein L is a leaving group.

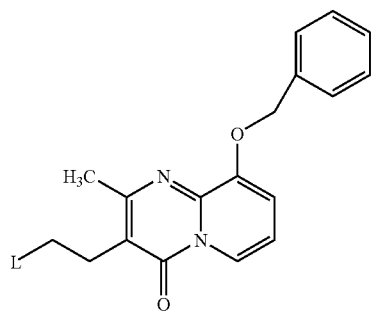

(IIIb)

Alternative leaving groups are well known to those skilled in the art. Such modified compounds, i.e., compounds of formula (IIIa) or (IIIb) may also be used in the processes described below.

The condensation may be carried out in the presence of a further solvent. Typically, the further solvent is an inert solvent selected from the group consisting of hydrocarbon solvents such as benzene, cyclohexane, toluene, or xylene; halogenated hydrocarbons such as chlorobenzene, methylene chloride; anisole; or DMF. Alternatively, the reaction may be performed in the absence of a further solvent.

The compound (III) obtained by the condensation is optionally purified for example by crystallization using solvents such as isopropyl alcohol, methanol, butanol, ethanol, ethyl acetate or mixtures thereof.

According to another aspect of the present invention, there is provided a process for preparing paliperidone or a salt thereof, the process comprising an intermediate step of condensing a 3-benzyloxy-2-aminopyridine (II) with an α-acyl lactone (V) to form a compound of formula (III) according to the process described above.

According to another aspect of the present invention, there is provided a process for preparing a compound of formula (IV) comprising reducing a compound of formula (III) to the compound of formula (IV).

acetic acid, dichloro acetic acid, trichloro acetic acid or formic acid; a mineral acid such as hydrochloric acid, sulfuric acid or phosphoric acid; and a Lewis acid such as boron trihalides. Preferably, the acid is acetic acid.

In an embodiment, the reduction is a catalytic reduction. The catalytic reduction may be carried out in the presence of a noble metal catalyst and hydrogen gas or using transfer hydrogenation.

In an embodiment, the catalyst is selected from the group consisting of palladium, palladium hydroxide, palladium on activated carbon, palladium on alumina, platinum, platinum on activated carbon, platinum dioxide and Raney nickel, preferably palladium-on-carbon. The catalyst may be a combination of catalysts.

In a particularly preferred embodiment, the amount of catalyst employed ranges from about 1% by weight of compound (III) to about 30% by weight of compound (III), preferably about 10% by weight of compound (III) to about 20% by weight of compound (III), more preferably the amount of catalyst is about 15% by weight of compound (III).

Suitably, the reaction is carried out in the presence of a solvent selected from: a lower alcohol solvent, for example, a $C_1$ to $C_3$ alcohol solvent such as methanol, ethanol, isopropanol or n-butanol; an ether such as tetrahydrofuran or 1,4-dioxane; an ester such as ethyl acetate; a halogenated hydrocarbon such as methylene dichloride, ethylene dichloride; a ketone such as acetone; or a mixture thereof.

In an embodiment, the compound of formula (III) is prepared by the process described above.

According to another aspect of the present invention, there is provided a process for preparing paliperidone or a salt thereof, the process comprising an intermediate step of reducing a compound of formula (III) to a compound of formula (IV) by the process described above.

According to another aspect of the present invention, there is provided a process for preparing paliperidone or a salt thereof comprising condensing chloroethyl derivative (IV) with compound (VI) or a salt thereof to obtain paliperidone (I), and optionally converting paliperidone to a salt thereof

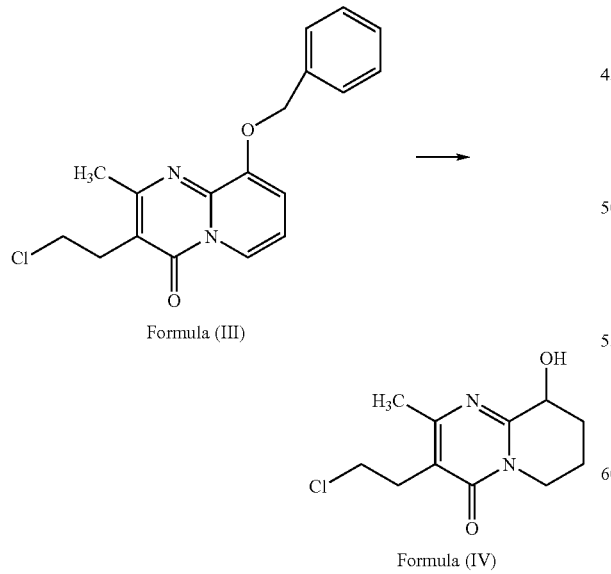

Formula (III)

Formula (IV)

Advantageously, the reduction is carried out in the presence of an acid. Suitably, the acid is selected from the group consisting of: a carboxylic acid such as acetic acid, trifluoro

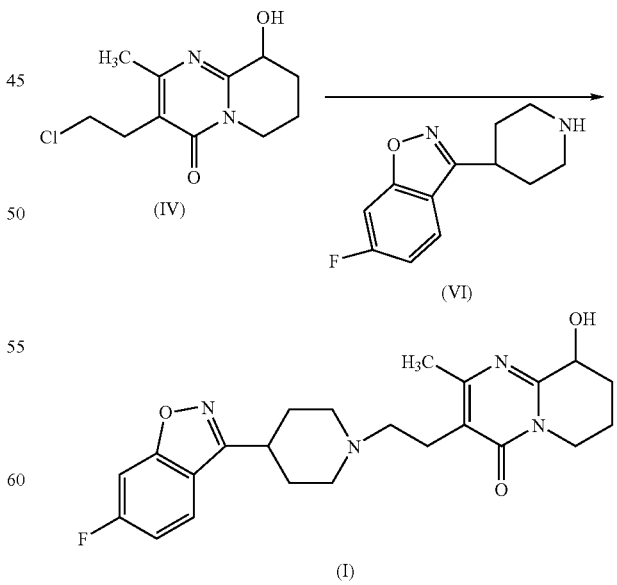

(IV)

(VI)

(I)

Preferably, the condensation is carried out in the presence of base. Suitably, the base is an organic base or an inorganic base. The base may be selected from the group consisting of pyridine, triethylamine, diisopropylethylamine, potassium phosphate, sodium carbonate, potassium carbonate, cesium carbonate, potassium bicarbonate, sodium bicarbonate, sodium hydroxide and potassium hydroxide, preferably potassium carbonate.

Typically, the condensation is carried out in an inert organic solvent, with or without water. In an embodiment, the solvent is a $C_1$ to $C_6$ straight chain alcohol, tetrahydrofuran, acetonitrile, DMF, DMA, methylene chloride, ethylene chloride, diglyme or toluene like. The preferred solvents are acetonitrile and methanol.

The condensation may be carried out at an elevated temperature. In an embodiment, the condensation is carried out at a temperature ranging from room temperature to the reflux temperature of the solvent, preferably from 40° C. to 90° C., more preferably from 75° C. to 80° C.

Optionally, the condensation is carried out in the presence of a catalyst such as tetrabutyl ammonium bromide, tetrabutyl ammonium chloride, potassium iodide, sodium iodide, sodium bromide, potassium bromide or lithium iodide.

The paliperidone is produced in a high purity (for example, not more than 1.50% total impurities, preferably not more than 1.00% total impurities) but may be further purified for example by crystallization using a solvent or a mixture of solvents.

The optional conversion of paliperidone to a salt thereof may be carried out according to any conventional process.

In an embodiment, compound (IV) is prepared by the process described above.

In an embodiment, there is provided a process for preparing paliperidone of formula (I) or a salt thereof.

Formula (I)

The process comprising: a) condensing 3-benzyloxy-2-aminopyridine (II) with an α-acyl lactone (V) in the presence of an activating agent and a catalytic amount of a dipolar aprotic solvent in a suitable inert solvent to obtain compound (III);

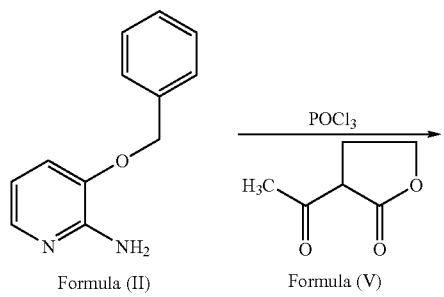

Formula (II)    Formula (V)

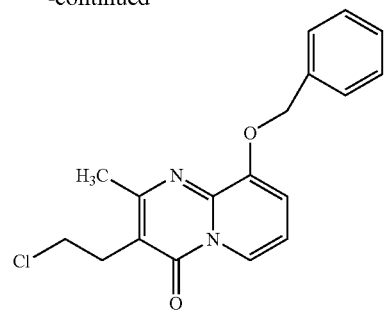

Formula (III)

b) reducing the compound of formula (III) in the presence of an acid to a compound of formula (IV);

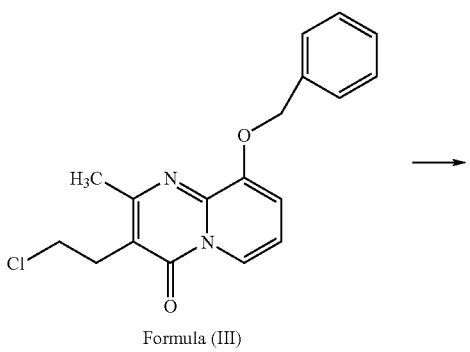

Formula (III)

Formula (IV)

c) condensing the chloroethyl derivative (IV) with compound (VI) or a salt thereof in the presence of a base to obtain paliperidone (I);

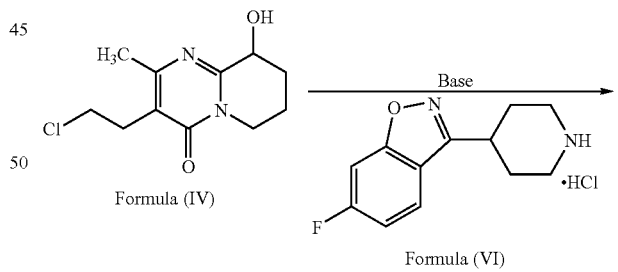

Formula (IV)    Formula (VI)

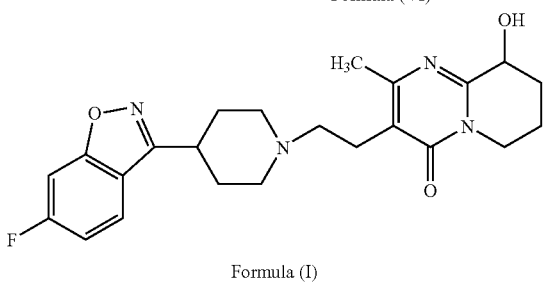

Formula (I)

and d) optionally converting paliperidone base to a pharmaceutically acceptable salt thereof.

According to another aspect of the present invention, there is provided a compound of formula (VIII). Compound of formula (VIII) is useful in the preparation of paliperidone of formula (I) or pharmaceutically acceptable salts thereof.

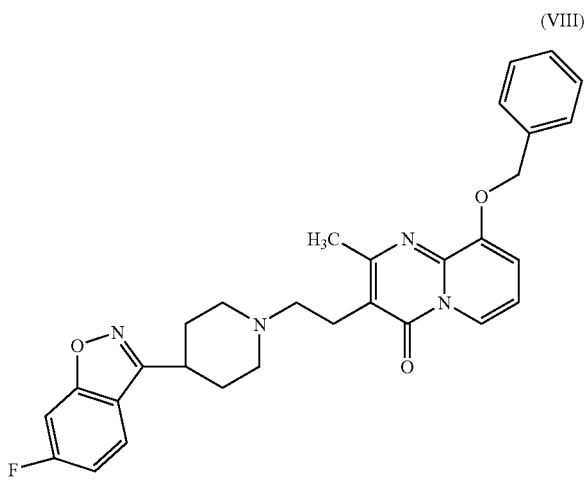

(VIII)

According to another aspect of the present invention, there is provided a process for preparing a compound of formula (VIII) comprising condensing a compound of formula (III) with a compound of formula (VI) or a salt thereof to obtain the compound of formula (VIII).

Typically, the condensation is carried out in the presence of a solvent. The solvent may be selected from the group consisting of toluene, ethyl acetate, acetonitrile, tetrahydrofuran, methylene chloride, ethylene chloride, diglyme, cyclohexane, N,N-dimethylformamide (DMF), N,N-dimethylacetamide (DMA), dimethylsulfoxide (DMSO), $C_1$ to $C_6$ straight or branched chain alcohols, such as methanol, ethanol, isopropanol, n-propanol, and mixtures thereof.

Preferably, the condensation is carried out in the presence of a base. The base may be an organic or inorganic base. The inorganic base may be selected from the group consisting of potassium carbonate, sodium carbonate, cesium carbonate, potassium bicarbonate, sodium bicarbonate, sodium hydroxide, potassium hydroxide, and potassium phosphate. The organic base may be selected from the group consisting of diisopropyl ethyl amine, pyridine and triethyl amine. Preferably, the base is potassium carbonate.

Optionally, the reaction is carried out in the presence of a catalyst. The catalyst may be selected from the group consisting of tetrabutyl ammonium bromide, tetrabutyl ammonium chloride, potassium iodide, sodium iodide, lithium iodide, sodium bromide, and potassium bromide; preferably potassium iodide.

In a preferred embodiment, the condensation is carried out in the presence of a base and a catalyst, more preferably in the presence of potassium carbonate and potassium iodide.

In an embodiment, the compound of formula (III) is prepared by the process described above.

According to another aspect of the present invention, there is provided a process for preparing paliperidone or a salt thereof comprising converting the compound of formula (VIII) to paliperidone and optionally converting the paliperidone to a salt thereof

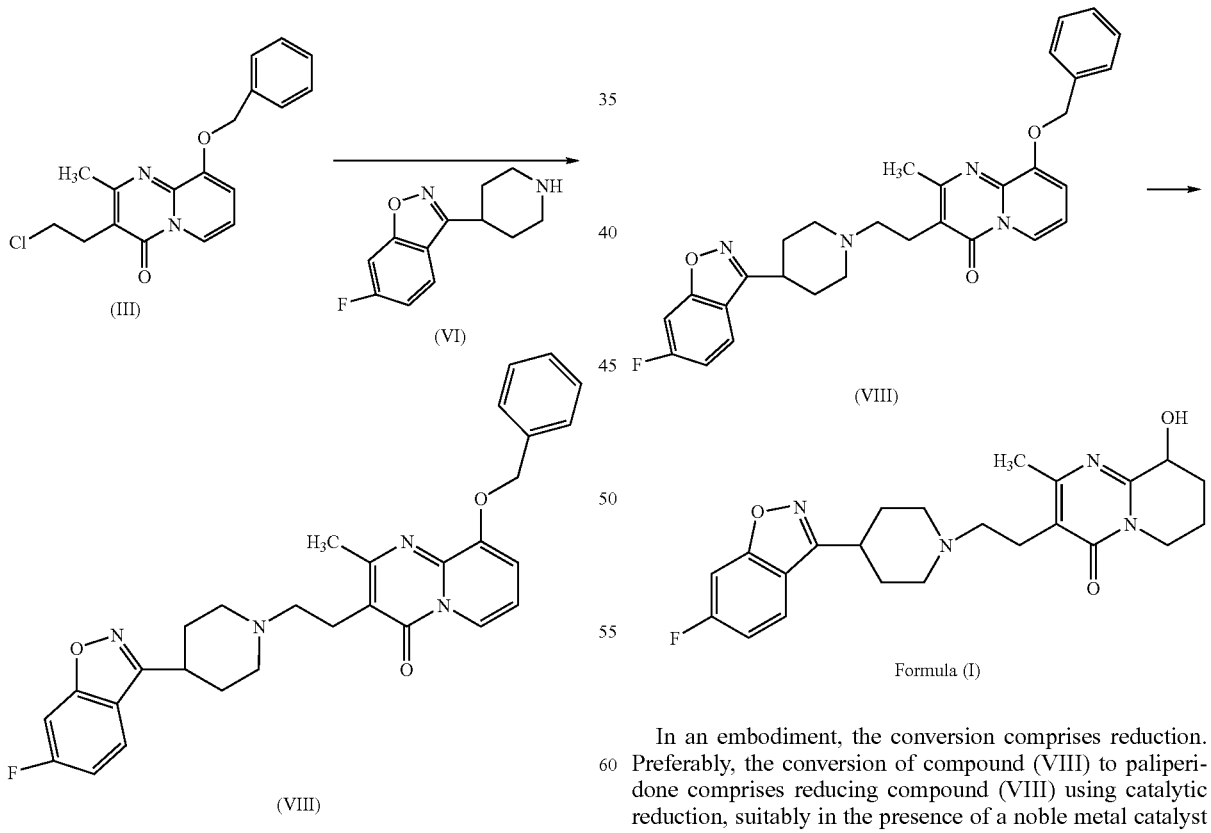

In an embodiment, the conversion comprises reduction. Preferably, the conversion of compound (VIII) to paliperidone comprises reducing compound (VIII) using catalytic reduction, suitably in the presence of a noble metal catalyst and hydrogen gas or using transfer hydrogenation.

In an embodiment, the catalyst is selected from the group consisting of palladium, palladium on carbon (preferably in an amount ranging from 1% to 20% of carbon by weight of palladium), platinum, platinum dioxide, platinum on carbon, palladium hydroxide, palladium on alumina or Raney nickel; preferably palladium on carbon (preferably 10% of carbon by weight of palladium) and the amount of catalyst employed ranges from 1% to 30% by weight of compound (VIII), preferably in an amount of 15% by weight of compound (VIII). In an embodiment, the catalytic reduction is carried out a temperature ranging from 20° C. to 80° C., preferably from 25° C. to 35° C. In another embodiment, the catalytic reduction may be carried out under a hydrogen gas pressure ranging from 1.0 Kg to 8.0 Kg, preferably from 4.0 Kg to 5.0 Kg. A combination of catalysts may also be used.

Typically, the reduction is carried out in the presence of a solvent. Preferably, the solvent is selected from the group consisting of ethyl acetate, methanol, ethanol, isopropyl alcohol, n-butanol, tetrahydrofuran, 1,4-dioxane, acetic acid, acetone, a halogenated hydrocarbon such as methylene dichloride or ethylene dichloride, or mixture thereof; preferably methanol.

Optionally, the paliperidone is converted to a salt thereof in accordance with conventional techniques.

In another embodiment, the compound of formula (VIII) has been prepared by the process described above.

In a preferred embodiment, there is provided a process for preparing paliperidone or a pharmaceutically acceptable salt thereof comprise the following steps: a) condensing 3-benzyloxy-2-aminopyridine of formula (II) with an α-acyl lactone of formula (V) in the presence of an activating agent, preferably phosphorus oxychloride, and a catalytic amount of dipolar aprotic solvent, and in the presence of a further solvent to obtain the compound of formula (III); b) condensing the compound of formula (III) with the compound of formula (VI) in the presence of a base and optionally in the presence of a catalyst to obtain the compound of formula (VIII); and c) reducing the compound of formula (VIII) to obtain paliperidone (I).

According to another aspect of the present invention, there is provided a compound of formula (X). Compound (X) is useful in the preparation of paliperidone of formula (I) or pharmaceutically acceptable salts thereof.

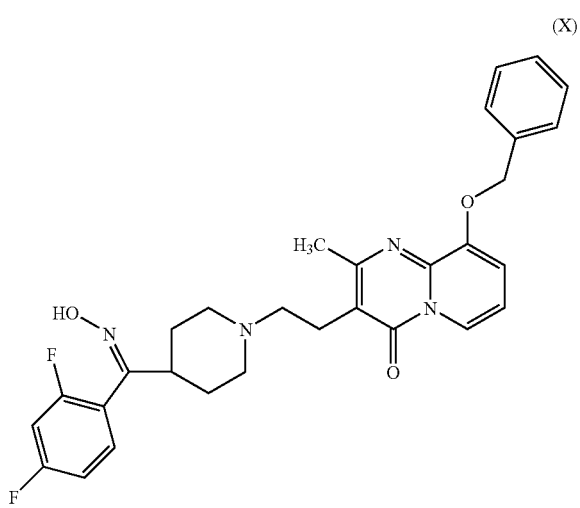

According to another aspect of the present invention, there is provided a process for preparing a compound of formula (X) comprising condensing a compound of formula (III) with a compound of formula (IX) to obtain the compound of formula (X).

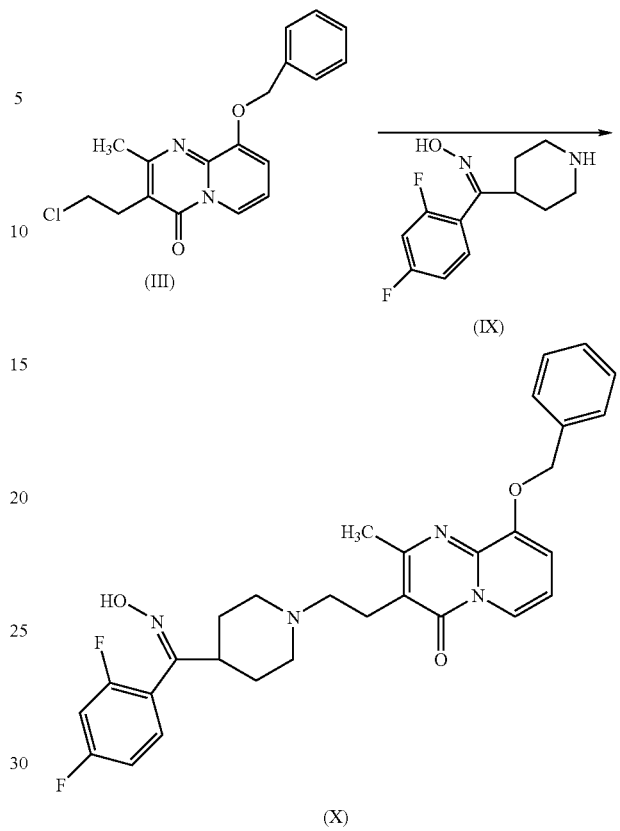

Typically, the condensation is carried out in the presence of a solvent. The solvent may be selected from the group consisting of toluene, ethyl acetate, acetonitrile, tetrahydrofuran, methylene chloride, ethylene chloride, diglyme, cyclohexane, N,N-dimethylformamide (DMF), N,N-dimethylacetamide (DMA), dimethylsulfoxide (DMSO), $C_1$ to $C_6$ straight or branched chain alcohols, such as methanol, ethanol, isopropanol, n-propanol, and mixtures thereof.

Preferably, the condensation is carried out in the presence of a base. The base may be an organic or inorganic base. The inorganic base may be selected from group the consisting of potassium carbonate, sodium carbonate, cesium carbonate, potassium bicarbonate, sodium bicarbonate, sodium hydroxide, potassium hydroxide and potassium phosphate. The organic base may be selected from the group consisting of diisopropyl ethyl amine, pyridine and triethyl amine. Preferably, the base is potassium carbonate.

Optionally, the reaction is carried out in the presence of a catalyst. The catalyst may be selected from the group consisting of tetrabutyl ammonium bromide, tetrabutyl ammonium chloride, potassium iodide, sodium iodide, lithium iodide, sodium bromide and potassium bromide; preferably potassium iodide.

In a preferred embodiment, the condensation is carried out in the presence of a base and a catalyst, more preferably in the presence of potassium carbonate and potassium iodide.

In an embodiment, the compound of formula (III) is prepared according to the process described above.

According to another aspect of the present invention, there is provided a process for preparing paliperidone or a salt thereof comprising converting the compound of formula (X) to paliperidone and optionally converting the paliperidone to the salt thereof

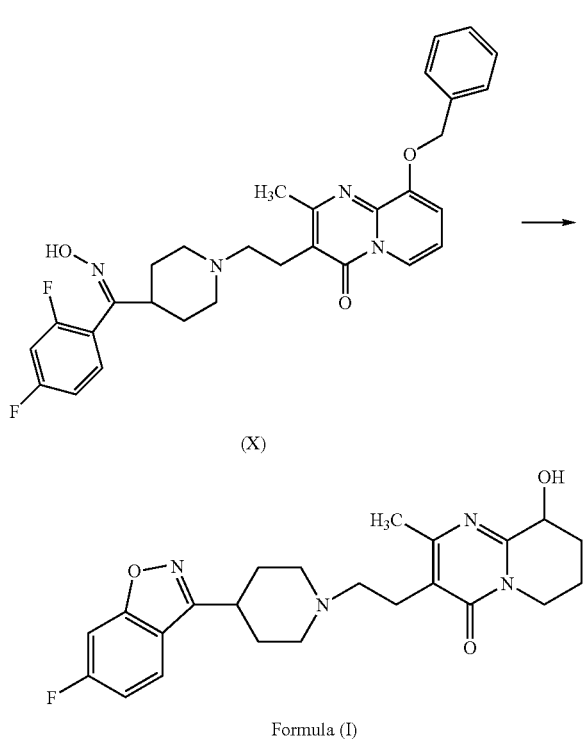

(X)

Formula (I)

In an embodiment, the conversion of compound (X) to paliperidone or a salt thereof comprises reducing the compound (X) to a compound of formula (XI) and cyclising the compound (XI) to obtain paliperidone.

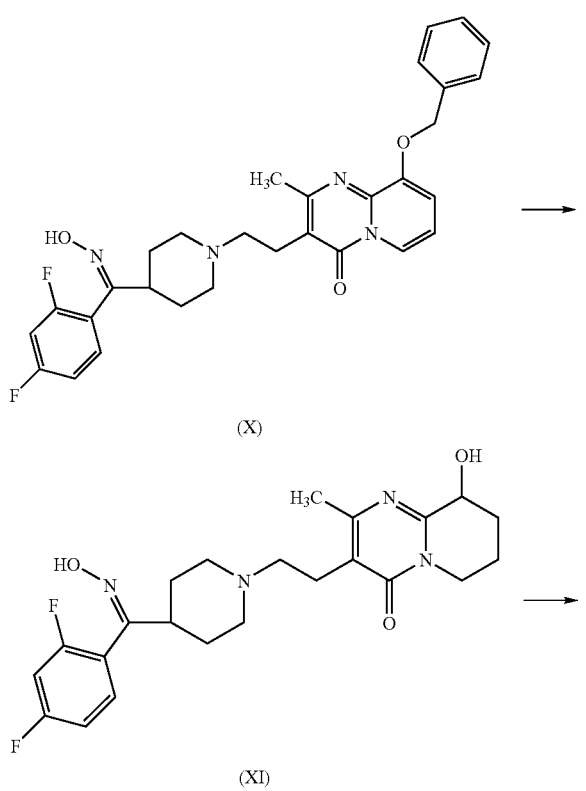

(X)

(XI)

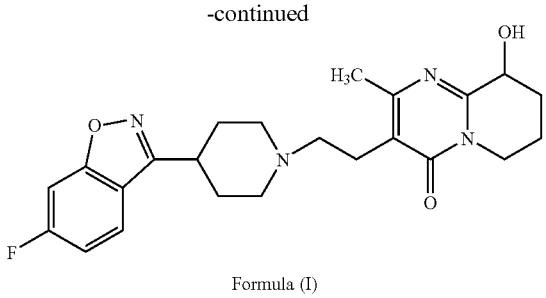

Formula (I)

Preferably, the reduction of compound (X) to compound (XI) comprises reducing compound (X) using catalytic reduction, suitably in the presence of a noble metal catalyst and hydrogen gas or using transfer hydrogenation.

In an embodiment, the catalyst is selected from the group consisting of palladium, palladium on carbon (preferably in an amount ranging from 1% to 20% of carbon by weight of palladium), platinum, platinum dioxide, platinum on carbon, palladium hydroxide, palladium on alumina or Raney nickel; preferably palladium on carbon (preferably in an amount of 10% of carbon by weight of palladium) and the amount of catalyst employed ranges from 1% to 30% by weight of compound (X), preferably 15% by weight of compound (X). In an embodiment, the catalytic reduction is carried out a temperature ranging from 20° C. to 80° C., preferably from 25° C. to 35° C. In another embodiment, the catalytic reduction may be carried out under a hydrogen gas pressure ranging from 1.0 Kg to 8.0 Kg, preferably from 4.0 Kg to 5.0 Kg. A combination of catalysts may also be used.

Typically, the reduction is carried out in the presence of a solvent. Preferably, the solvent is selected from the group consisting of ethyl acetate, methanol, ethanol, isopropyl alcohol, n-butanol, tetrahydrofuran, 1,4-dioxane, acetic acid, acetone, a halogenated hydrocarbon such as methylene dichloride or ethylene dichloride, or mixture thereof; preferably methanol.

The cyclisation of compound (XI) may be carried out in a solvent such as N,N-dimethylformamide, N,N-dimethylacetamide, dimethylsulfoxide, toluene, xylene, anisole, tetrahydrofuran, ethyl acetate, acetonitrile, methyl isobutyl ketone or methyl ethyl ketone, preferably toluene.

The cyclisation reaction is preferably carried out in the presence of an inorganic base such as potassium carbonate, sodium carbonate, potassium bicarbonate, sodium bicarbonate, cesium carbonate, lithium carbonate, sodium hydroxide or potassium hydroxide; preferably potassium carbonate.

Optionally, the cyclisation reaction is carried out in the presence of a catalyst such as potassium iodide, sodium iodide, lithium iodide, sodium bromide or potassium bromide; preferably potassium iodide.

Optionally, the paliperidone is converted to a salt thereof in accordance with conventional techniques.

In another embodiment, the compound of formula (X) has been prepared by the process described above.

In a preferred embodiment, there is provided a process for preparing paliperidone or a pharmaceutically acceptable salt thereof comprise the following steps: a) condensing the compound of formula (III) with the compound of formula (IX) in the presence of base to obtain the compound of formula (X); b) reducing the compound of formula (X) to obtain the compound of formula (XI); and c) cyclising the compound of formula (XI) to obtain paliperidone of formula (I).

In all aspects of the present invention in which paliperidone is optionally converted to a salt thereof, the salt is an acid addition salt formed by treatment with an appropriate acid, such as a hydrohalic acid, for example hydrochloric or hydrobromic acid, sulfuric acid, nitric acid, phosphoric acid, acetic acid, propanoic acid, hydroxyacetic acid, 2-hydroxypropanoic acid, 2-oxopropanoic acid, ethanedioic acid, propanedioic acid, butanedioic acid, (Z)-2-butenedioic acid, (E)-2-butenedioic acid, 2-hydroxybutanedioic acid, 2,3-dihydroxybutanedioic acid, 2-hydroxy-1,2,3-propanetricarboxylic acid, methanesulfonic acid, ethanesulfonic acid, benzenesulfonic acid, 4-methylbenzenesulfonic acid, cyclohexanesulfamic acid, 2-hydroxybenzoic acid or 4-amino-2-hydroxybenzoic acid.

According to another aspect of the present invention, there is provided paliperidone or a salt thereof prepared according to any one of the processes described above. According to another aspect of the present invention, there is provided a pharmaceutical composition comprising paliperidone or a salt thereof prepared according to any one of the processes described above and one or more pharmaceutically acceptable excipients. Such pharmaceutical compositions and excipients are well known to those skilled in the art. According to another aspect of the present invention, there is provided the use of paliperidone or a salt thereof prepared according to any one of the processes described above in medicine. According to another aspect of the present invention, there is provided the use of paliperidone or a salt thereof prepared according to any one of the processes described above in the treatment of schizophrenia or bipolar disorder. According to another aspect of the present invention, there is provided a method of treating schizophrenia or bipolar disorder comprising administering to a patient in need thereof a therapeutically effective amount of paliperidone or a salt thereof prepared according to any one of the processes described above.

DETAILED DESCRIPTION OF THE INVENTION

In one aspect, the present invention relates to novel key intermediates useful in the synthesis of paliperidone or its pharmaceutically acceptable salts. One of the novel compounds has the formula (VIII).

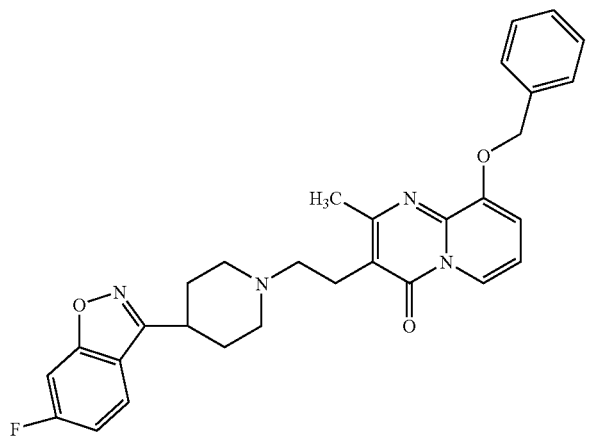

(VIII)

In an embodiment, the present invention provides a process for the preparation of paliperidone or a pharmaceutically acceptable salt thereof, which comprises the following step:

a) condensing 3-benzyloxy-2-aminopyridine of formula (II) with an α-acyl lactone of formula (V) in the presence of an activating agent and catalytic amount of dipolar aprotic solvent, in a suitable inert solvent and at suitable temperature, to obtain compound of formula (III).

It was found that by use of catalytic amount of dipolar aprotic solvent, the formation of impurities was minimized to about 5%. Typically, such dipolar aprotic solvent is selected from group comprising of N,N-dimethylformamide (DMF), N,N-dimethylacetamide (DMA), dimethylsulfoxide (DMSO), 1-methyl-2-pyrrolidinone, pyridine, acetic anhydride, preferably DMF.

Appropriate activating agent used for the condensation reaction in step a) is halogenating agent selected from group comprising of thionyl chloride, phosphorous oxychloride, phosphorous trichloride, phosphorous pentachloride, oxalyl chloride, phosgene and the like. In particular, phosphorous oxychloride is preferred.

Suitable inert solvent for the condensation reaction include hydrocarbon solvents such as benzene, cyclohexane, toluene, or xylene; halogenated hydrocarbons such as chlorobenzene, methylene chloride; anisole or DMF. Alternatively, the reaction may also be performed in the absence of solvent.

In an attempt to determine which possible initial impurities could cause the large scale deviation, it was observed that by carrying reaction as reported in the prior art, at high temperature of 90° C. and adding compound (V) in lots, yields 50% of undesired impurities which impair the desire reaction product.

The suitable temperature at which reaction is carried out ranges from 50° C. to 100° C., preferably 60 to 80° C. The reaction is carried out for 1 to 20 hours, preferably for 10 to 15 hours by which the undesired impurity is reduced substantially.

The product obtained is optionally purified by crystallization using solvents selected from group comprising of isopropyl alcohol, methanol, butanol, ethanol, ethyl acetate or mixtures thereof.

In a further embodiment, the process for the preparation of paliperidone or a pharmaceutically acceptable salt thereof, comprises the following step:

b) condensing compound of formula (III) with compound of formula (VI) or a salt thereof in a suitable solvent and in presence of a base to give novel intermediate of formula (VIII). Optionally, the reaction is carried out in presence of a catalyst.

The suitable solvent used is selected from group comprising of toluene, ethyl acetate, acetonitrile, tetrahydrofuran, methylene chloride, ethylene chloride, diglyme, cyclohexane, N,N-dimethylformamide (DMF), N,N-dimethylacetamide (DMA), Dimethylsulfoxide (DMSO), $C_1$ to $C_6$ straight or branched chain alcohols such as, but not limited to, methanol, ethanol, isopropanol, n-propanol or mixtures thereof.

The base used is organic or inorganic. Inorganic base is selected from group comprising of potassium carbonate, sodium carbonate, cesium carbonate, potassium bicarbonate, sodium bicarbonate, sodium hydroxide, potassium hydroxide, potassium phosphate while organic base is selected from, but not limited to, diisopropyl ethyl amine, pyridine, triethyl amine. The base preferred is potassium carbonate.

The catalyst is selected from group comprising of tetrabutyl ammonium bromide, tetrabutyl ammonium chloride, potassium iodide, sodium iodide, lithium iodide, sodium bromide, potassium bromide; preferably potassium iodide.

In a further embodiment, the process for the preparation of paliperidone or a pharmaceutically acceptable salt thereof, comprises the following step:

c) reducing intermediate of formula (VIII) using catalytic reduction in the presence of a noble metal catalyst and hydrogen gas or using transfer hydrogenation to obtain paliperidone of formula (I).

Preferred catalysts used are those known in the art such as palladium, palladium on carbon (preferably in an amount ranging from 1% to 20% carbon by weight of palladium), platinum, platinum dioxide, platinum on carbon, palladium hydroxide, palladium on alumina, Raney nickel, preferably palladium on carbon (preferably in an amount of 10% carbon by weight of palladium) and the amount of catalyst employed ranges from 1% to 30% by weight of compound (VIII), preferably 15% by weight of compound (VIII). In an embodiment, the process is carried out in a suitable solvent at a temperature ranging from 20-80° C., preferably 25-35° C. under hydrogen gas pressure ranging from 1.0-8.0 Kg, preferably 4.0-5.0 Kg.

A combination of catalysts may also be used. The amount of catalyst employed is reduced to about 15% w/was compared to 60% w/was reported in the prior art. This obviates the need for handling large quantity of catalyst on industrial scale, thereby reducing the risk involved.

The suitable solvent used is selected from group comprising of ethyl acetate, methanol, ethanol, isopropyl alcohol, n-butanol, tetrahydrofuran, 1,4-dioxane, acetic acid, acetone, halogenated hydrocarbons such as methylene dichloride, ethylene dichloride or mixture thereof, preferably methanol.

Optionally, paliperidone base can be converted to pharmaceutically acceptable salts thereof. Such conversions are well known to those skilled in the art and involve treatment with an acid to form an acid addition salt.

The process is represented by the Scheme I as follows:

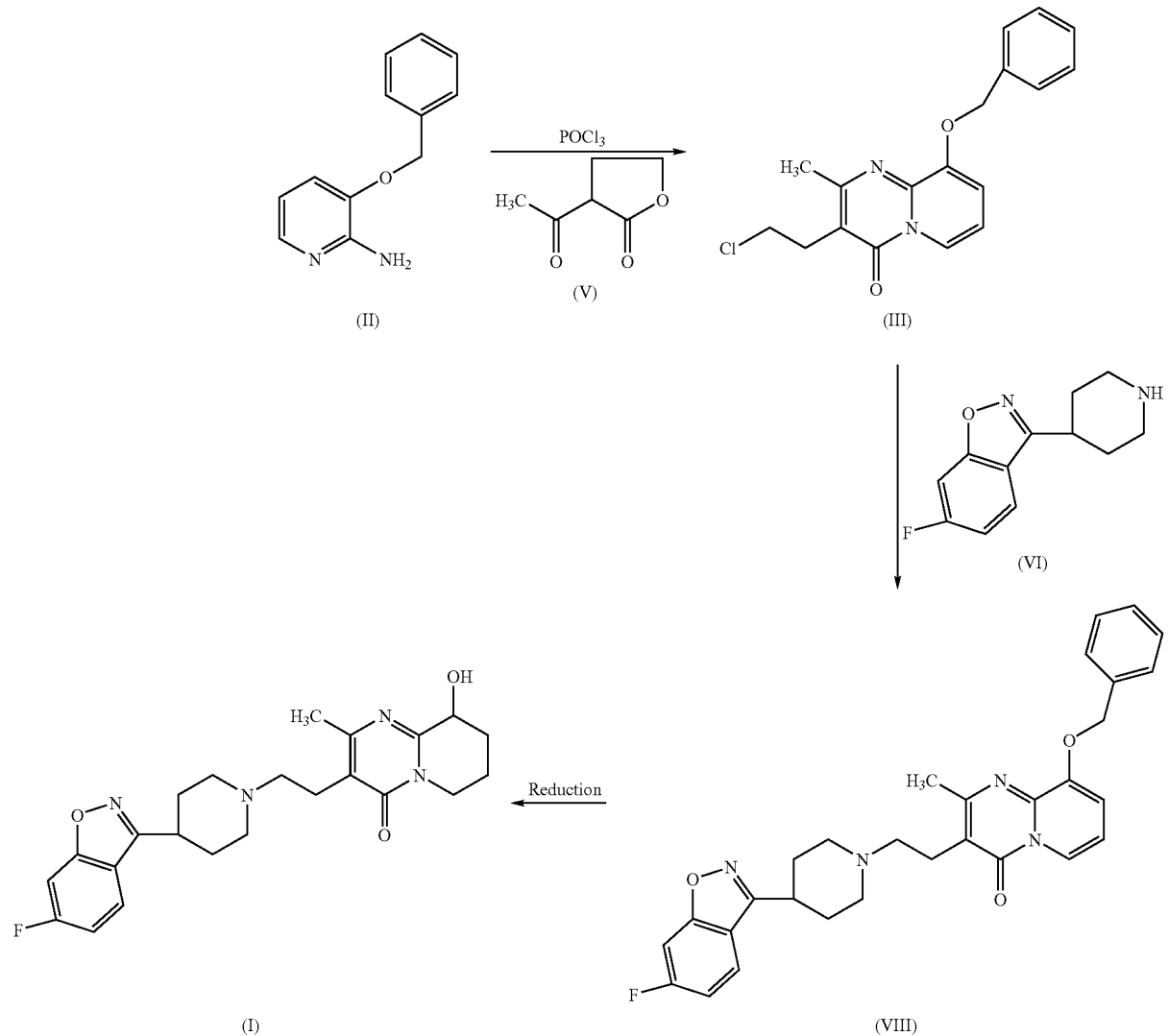

In another aspect of the present invention, there is provided a compound of formula (X) which is useful in the synthesis of paliperidone or its pharmaceutically acceptable salts.

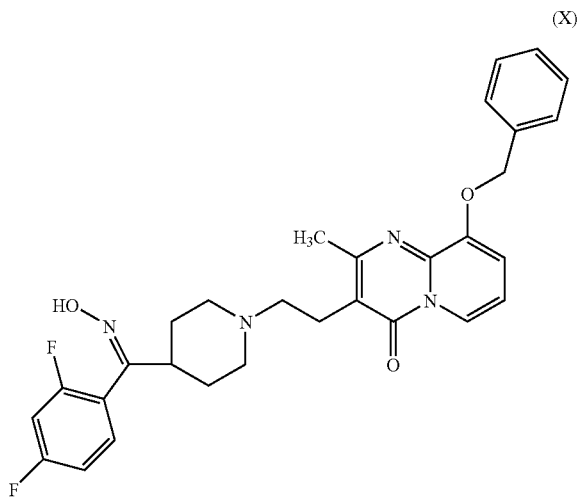

(X)

This compound of formula (X) may be used as an intermediate in a process for the preparation of paliperidone or a salt thereof. The process may comprise the following steps: a) condensing a compound of formula (III) with a compound of formula (IX) in a suitable solvent and in the presence of a base to obtain a compound of formula (X); b) reducing the compound of formula (X) to obtain a compound of formula (XI); c) cyclising the compound of formula (XI) to obtain paliperidone of formula (I); and d) optionally converting the paliperidone of formula (I) to a salt thereof.

The compound of formula (III) may be prepared by the process mentioned above.

The base and solvent used for the preparation of compound (X) may be the same as those used in step b) above for Scheme I. Optionally, the preparation of compound (X) is carried out in the presence of a catalyst. The catalyst may be the same as that used in step b) above for Scheme I.

The compound of formula (X) may be reduced using a noble metal catalyst and hydrogen gas or using transfer hydrogenation under the conditions mentioned in step c) above for Scheme I, to obtain the compound of formula (XI).

The compound of formula (XI) may be cyclised in a solvent such as N,N-dimethylformamide, N,N-dimethylacetamide, dimethylsulfoxide, toluene, xylene, anisole, tetrahydrofuran, ethyl acetate, acetonitrile, methyl isobutyl ketone or methyl ethyl ketone, preferably toluene.

The reaction may be carried out in the presence of an inorganic base such as potassium carbonate, sodium carbonate, potassium bicarbonate, sodium bicarbonate, cesium carbonate, lithium carbonate, sodium hydroxide or potassium hydroxide preferably potassium carbonate.

Optionally, the reaction is carried out in the presence of a catalyst such as but not limited to potassium iodide, sodium iodide, lithium iodide, sodium bromide or potassium bromide, preferably potassium iodide.

The process may be represented by following reaction Scheme II:

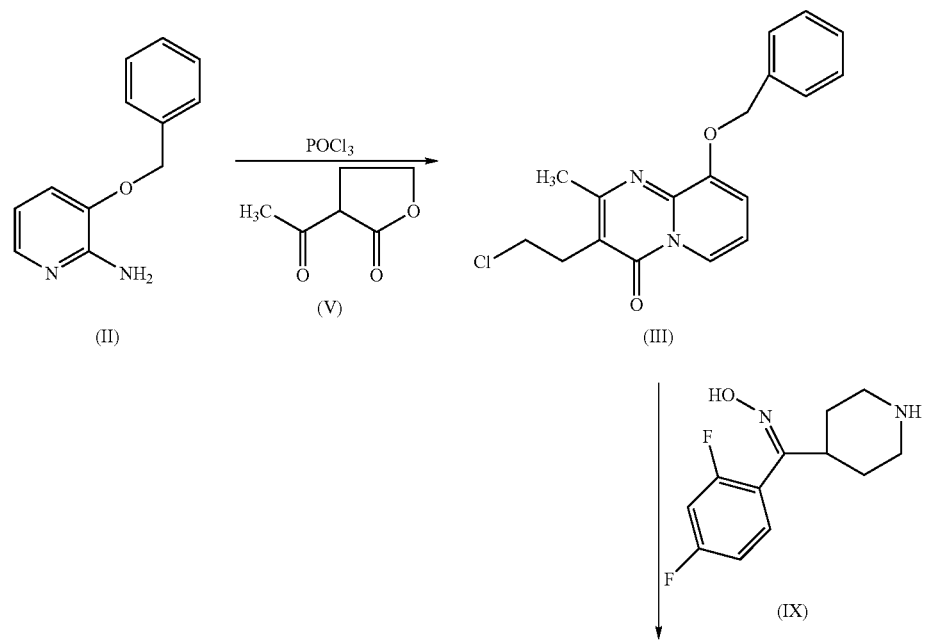

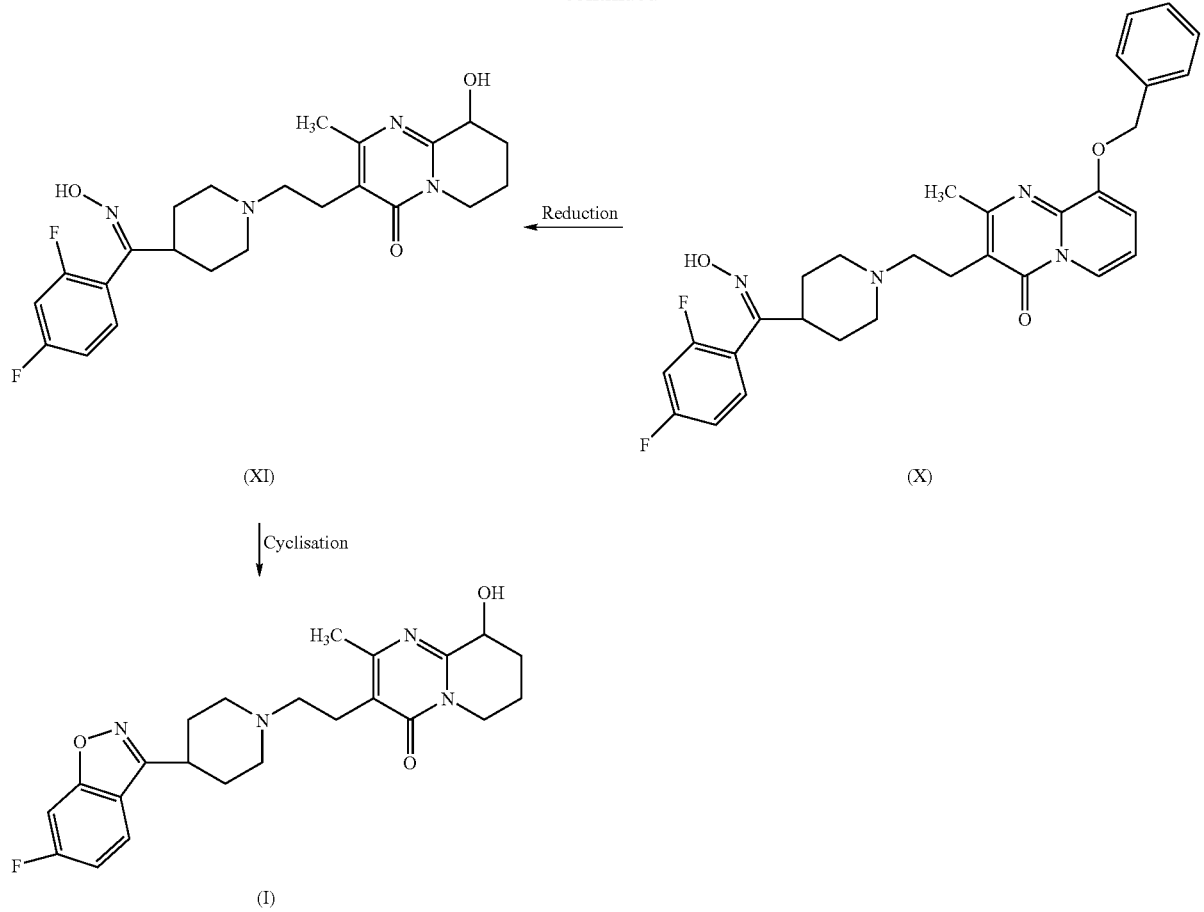

In yet another embodiment of the invention, there is provided a process for the preparation of paliperidone or a pharmaceutically acceptable salt thereof. The process may comprise the step of: i) catalytically reducing the compound of formula (III) using a noble metal catalyst and hydrogen gas or using transfer hydrogenation under to obtain chloroethyl derivative of formula (IV).

The conditions used for reduction may be the same as those used in step c) above for Scheme I. The reaction may be carried out in the presence of an acid.

In the process of the present invention, an acid may be employed to reduce the formation of the des-chloro impurity of formula (VII). Typically, this step results in a reduction of the des-chloro impurity to less than 3%. The acid used may be selected from a carboxylic acid such as acetic acid, trifluoro acetic acid, dichloro acetic acid, trichloro acetic acid, formic acid; a mineral acid such as hydrochloric acid, sulfuric acid, phosphoric acid; or a Lewis acid such as boron trihalide and the like. In particular, acetic acid is preferred.

The reaction may be carried out in lower alcohol solvents for example $C_1$ to $C_3$ alcohol solvents such as methanol, ethanol, isopropanol or n-butanol; ethers such as tetrahydrofuran, 1,4-dioxane; esters such as ethyl acetate; halogenated hydrocarbons; ketones such as acetone or a mixture of such solvents.

The process of this invention has been found to be particularly advantageous over the prior art US '952 process. This prior art process requires large volumes of solvent such as methanol, and a catalyst such as 10% of palladium on charcoal (60% w/w) which tends to produce a significant amount of des-chloro impurity of formula (VII). The deschloro impurity formed not only leads to incomplete reaction but also lowers the yield of the desired product.

The compound of formula (III) may be prepared by the process mentioned in step a) above for Scheme I.

The process for preparing paliperidone or salt thereof may comprise condensing a chloroethyl derivative of formula (IV) with a compound of formula (VI) or a salt thereof in the presence of a base and at an elevated temperature to obtain paliperidone of formula (I).

The base used may be the same as that used in step b) above for Scheme I.

In an embodiment, the reaction temperature ranges from room temperature to the reflux temperature of the solvent, preferably from 40° C. to 90° C.

This reaction is typically carried out in an inert, organic solvent, with or without water. Appropriate organic solvents are $C_1$ to $C_6$ straight chain alcohols, tetrahydrofuran, acetonitrile, DMF, DMA, methylene chloride, ethylene chloride, diglyme, toluene and the like. The preferred solvents are acetonitrile and methanol.

Optionally, the reaction is carried out in presence of a catalyst. The catalyst used may be the same as that used in step b) above for Scheme I.

Paliperidone obtained by following the processes of the present invention advantageously has a reduced amount of the des-chloro impurity, to the extent that, in a particularly preferred embodiment, the impurity is not detected. In another particularly preferred embodiment, paliperidone obtained by following the processes of the present invention is substantially free of all impurities. By "substantially free of," it is meant that the paliperidone contains no more than 1.50% total impurities, preferably, no more than 1.00% total impurities. To achieve an even higher purity paliperidone product, the paliperidone prepared according to the processes of the present invention may be further purified by crystallization using a solvent or mixture of solvents.

Optionally, paliperidone base may be converted to a pharmaceutically acceptable salt thereof. Such conversions are well known to those skilled in the art and involve treatment with an acid to form an acid addition salt.

The process may be represented by the following Scheme III:

The contents were heated slowly to 50-55° C. and maintained for 30 minutes. A solution of compound (V) in toluene (84 ml in 100 ml) was added slowly to the reaction mass and the reaction mass was heated to 70-75° C., maintained for 30 minutes. The reaction mass was further heated to 80-85° C., maintained for 6-7 hours. After completion of the reaction, the reaction mass was cooled to room temperature, quenched into ice-water mixture (1000 ml) and extracted with methylene chloride (250 ml×2). The methylene chloride layer was washed with water (250 ml×2). To this water (50 ml) was charged and pH of the reaction mass was adjusted to 7.0-7.5 using triethylamine. The organic layer was separated and dried over sodium sulphate (5 g) and distilled off completely under vacuum below 35° C. The residue obtained was dissolved in isopropyl alcohol (85 ml) at 40-45° C., cooled to

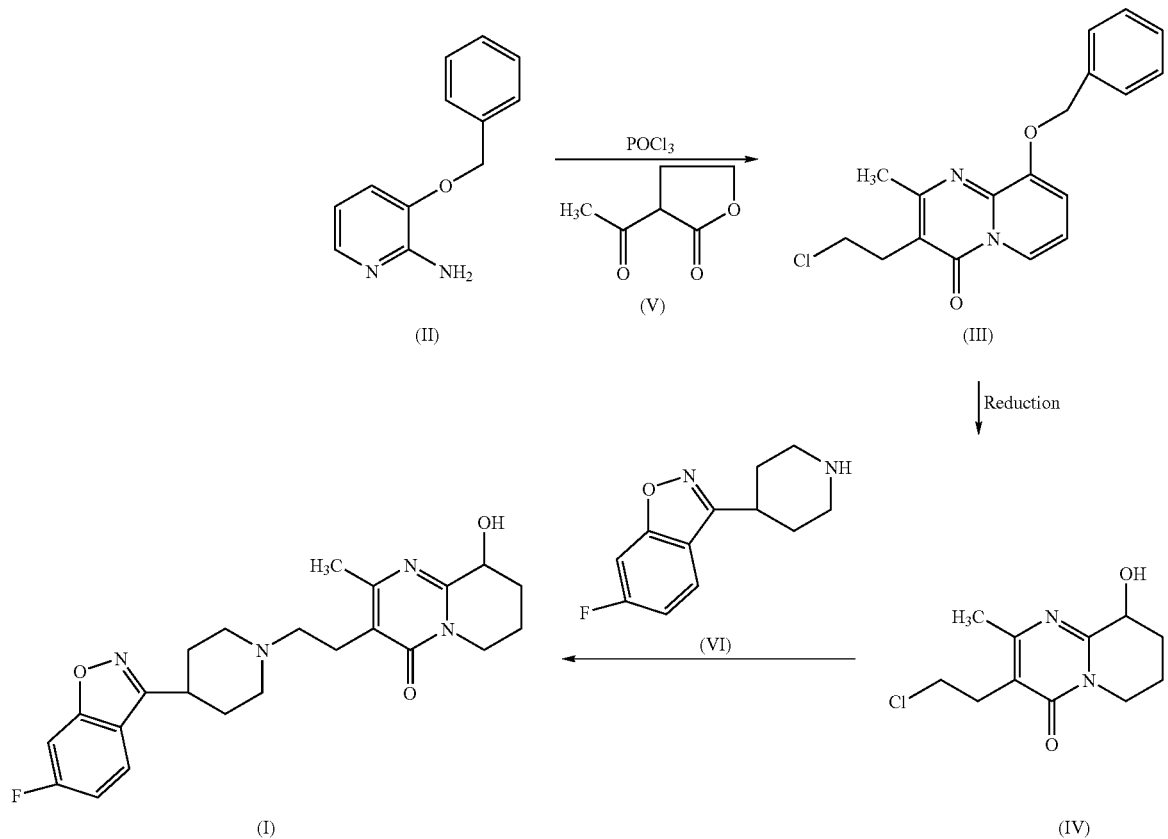

Scheme III

EXAMPLES

The present invention is now further illustrated by the following examples, which do not, in any way, limit the scope of the invention.

Example 1

Preparation of Compound of Formula (III)

To a three-necked flask compound (II) (50 g) and toluene (500 ml) were charged. The reaction mixture was cooled to 0-5° C. To this solution dimethyl formamide (5.0 ml) was added followed by slow addition of freshly distilled phosphorus oxychloride (105 ml) at 0-5° C. over a period of 2 hours.

0-5° C., filtered, washed with chilled isopropyl alcohol (20 ml) and dried under vacuum at 40-45° C. for 6 hours to yield compound (III) (52.5 g), HPLC purity-99%).

Example 2

Preparation of Compound of Formula (IV)

Compound (III) (20 g), ethylacetate (1500 ml) and acetic acid (60 ml) were charged in a hydrogenator. To this 10% palladium on carbon (5 g) was added and the reaction mass was hydrogenated by applying hydrogen gas pressure of 3.5-4.0 Kg at 25-30° C. for 15 hours to yield 14.5 g of compound (IV) (HPLC purity-90%).

Example 3

Preparation of Compound of Formula (I) [Paliperidone]

In a three necked flask acetonitrile (230 ml), compound (IV) (20 g) and compound (VI) (23.3 g) were charged. To the reaction mass, potassium carbonate (18 g) and potassium iodide (0.5 g) were added. The contents were heated to 76-78° C. and maintained for 3 hours at 76-78° C. After completion of reaction, the reaction mixture was cooled to 0-5° C. and stirred for 1 hour. The solid, was filtered, washed with water (65 ml). The solid obtained was dissolved in methanol (190 ml) by heating the contents to 60-65° C., treated with activated charcoal (3.5 gm), stirred at 60-65° C. for 30 minutes. The reaction mass was filtered hot over hyflo at 60-65° C., washed with hot methanol (20 ml). Methanol was distilled completely under vacuum below 45° C. to obtain residue. Ethyl acetate (20 ml) was charged and continued distillation under vacuum to remove traces of methanol. The residue was stirred in (20 ml) ethyl acetate for 1 hour at 25-30° C. The resulting solid was filtered and washed with ethyl acetate (10 ml) and dried under vacuum at 40-45° C. for 6 hours to yield 6.5 g of paliperidone. (HPLC purity-99.5%).

Example 4

Preparation of Compound of Formula (VIII)

Acetonitrile (1000 ml), compound of formula (III) (50 g), compound of formula (VI) (39 g), potassium carbonate (50 g) and potassium iodide (5 g) were charged and refluxed for 20 hours. The reaction mass was cooled to room temperature, chilled to 0-5° C., filtered, washed with water (100 ml) and then dissolved in methanol (200 ml) by heating the contents to 60-65° C., treated with activated charcoal (4.0 g), stirred at 60-65° C. for 30 minutes. The reaction mass was filtered hot over hyflo at 60-65° C., washed with hot methanol (50 ml). Methanol was distilled under vacuum below 45° C. to obtain residue, ethyl acetate (50 ml) was charged and stripped out methanol. The residue was stirred in ethyl acetate (50 ml) for 1 hour at 25-30° C. The material so obtained was filtered, washed with ethyl acetate (20 ml) and dried under vacuum at 40-45° C. for 6 hours to yield compound of formula (VIII) (50 g).

Example 5

Preparation of Compound of Formula (I)

Methanol (1000 ml), compound of formula (VIII) (35 g) and 10% palladium on carbon (5 g) were charged and hydrogenated at hydrogen gas pressure of 4.5-5.0 Kg at 30-35° C. for 6 hours. The reaction mass was filtered, the clear filtrate was concentrated. Isopropanol (200 ml) was charged, stirred for 30 minutes at 5-10° C. The material was filtered, washed with chilled isopropanol (20 ml) and was dissolved in methanol (200 ml) at 60-65° C. The reaction mass was treated with activated charcoal (4 g), stirred for 30 minutes, filtered over hyflo when hot, washed with hot methanol (25 ml). The clear filtrate was distilled completely under vacuum below 45° C., methanol was stripped off with ethyl acetate (25 ml). The residue was stirred in ethyl acetate (30 ml) for 1 hour at 25-30° C. The material was filtered, washed with ethyl acetate (15 ml) and dried under vacuum at 40-45° C. to yield paliperidone, compound of formula (I) (15.0 g).

Example 6

Preparation of Compound of Formula (X)

Dimethyl formamide (500 ml), compound of formula (III) (50 g), compound of formula (IX) (44 g), potassium carbonate (50 g) and potassium iodide (5 g) were charged and heated to 90-95° C. for 5 hours. The reaction mass was quenched into water (400 ml), extracted with methylene chloride (500 ml×3). Methylene chloride layer was washed with water (200 ml×3), dried over sodium sulphate (5 g), concentrated to residue. Isopropanol (200 ml) was added, cooled to 5-10° C., filtered and washed with chilled isopropanol (50 ml) and dried at 40-45° C. to yield compound of formula (X) (50.0 g).

Example 7

Preparation of Compound of Formula (XI)

Ethyl acetate (1000 ml), compound of formula (X) (40 g) and 10% palladium on carbon (5 g) were charged and hydrogenated at hydrogen gas pressure of 4.5-5.0 Kg at 30-35° C. for 4 hours. The reaction mass was filtered, the clear filtrate was concentrated. Isopropanol (200 ml) was charged, stirred for 30 minutes at 5-10° C., filtered and washed with chilled isopropanol (20 ml) and dried at 45-50° C. to yield compound of formula (XI) (18 g).

Example 8

Preparation of Compound of Formula (I)

Toluene (500 ml), compound of formula (XI) (50 g) and potassium carbonate (5 g) were charged and heated to reflux for 4 hours. The reaction mass was cooled to 5-10° C., filtered, washed with chilled toluene (50 ml). The filtered material was dissolved in methylene chloride (500 ml), washed with water (250 ml×2). Methylene chloride layer was dried with sodium sulphate (5 g), concentrated to residue. Isopropanol (200 ml) was charged, stirred for 30 minutes at 5-10° C., filtered and washed with chilled isopropanol (40 ml). The material was dissolved in methanol (200 ml) at 60-65° C., treated with activated charcoal (4 g), stirred for 30 minutes, filtered over hyflo when hot, washed with hot methanol (25 ml). The clear filtrate was distilled completely under vacuum below 45° C. and methanol was stripped off with ethyl acetate (25 ml). The residue was stirred in ethyl acetate (30 ml) for 1 hour at 25-30° C. The material was filtered, washed with ethyl acetate (15 ml) and dried under vacuum at 45-50° C. to yield paliperidone, compound of formula (I) (38.0 g).

It will be appreciated that the invention may be modified within the scope of the appended claims.

The invention claimed is:

1. A process for preparing paliperidone or a pharmaceutically acceptable salt thereof comprising:
   (a) condensing a 3-benzyloxy-2-aminopyridine derivative (II) with an α-acyl lactone (V) in the presence of a catalytic amount of a dipolar aprotic solvent and an activating agent to obtain a compound of formula (III);

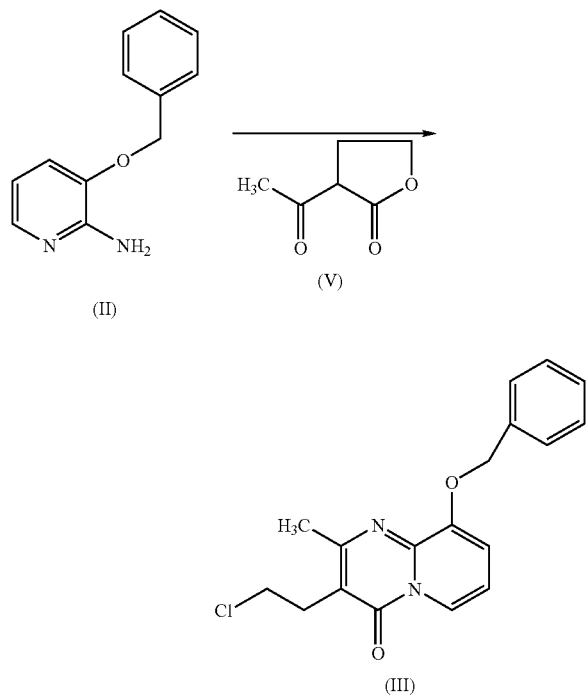

(b) condensing the compound of formula (III) with a compound of formula (IX) to obtain a compound of formula (X);

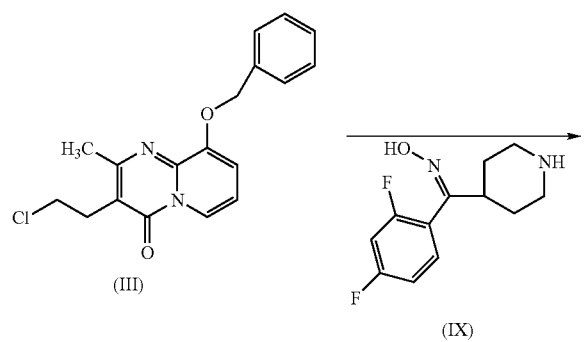

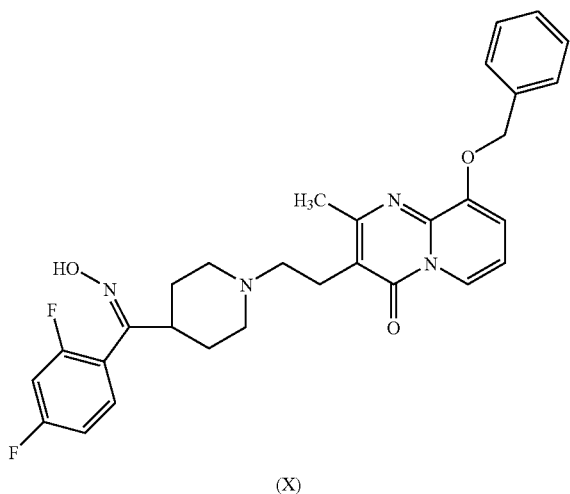

(c) converting the compound (X) to a compound of formula (XI) by catalytic reduction and cyclising the compound (XI) to obtain paliperidone;

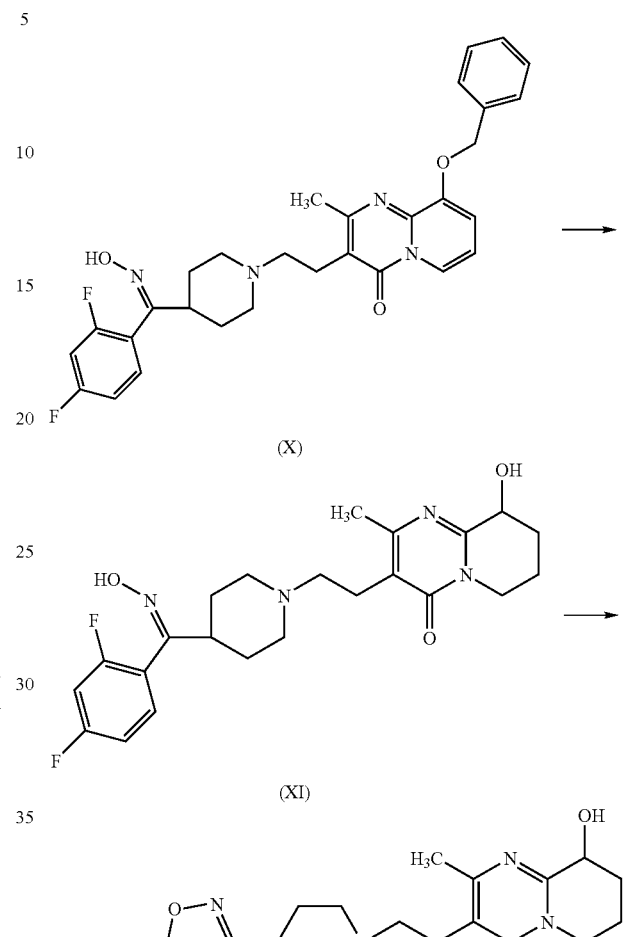

(d) and optionally converting paliperidone to a pharmaceutically acceptable salt thereof.

2. The process according to claim 1, wherein the dipolar aprotic solvent is selected from the group consisting of N,N-dimethylformamide (DMF), N,N-dimethylacetamide (DMA), dimethylsulfoxide (DMSO), 1-methyl-2-pyrrolidinone, pyridine and acetic anhydride.

3. The process according to claim 1, wherein the activating agent is a halogenating reagent selected from the group consisting of thionyl chloride, phosphorous oxychloride, phosphorous trichloride, phosphorous pentachloride, oxalyl chloride and phosgene.

4. The process according to claim 1, wherein the catalytic reduction is carried out in the presence of a noble metal catalyst and hydrogen gas or using transfer hydrogenation.

5. The process according to claim 4, wherein the catalyst is selected from the group consisting of palladium, palladium hydroxide, palladium on activated carbon, palladium on alumina, platinum, platinum dioxide, platinum on activated carbon and Raney nickel.

6. The process according to claim 1, wherein step (b) is carried out in the presence of a base selected from the group consisting of potassium carbonate, sodium carbonate, cesium carbonate, potassium bicarbonate, sodium bicarbonate, sodium hydroxide, potassium hydroxide, potassium phosphate, diisopropyl ethyl amine, pyridine and triethyl amine.

7. The process according to claim 1, wherein step (b) is carried out in the presence of a catalyst selected from the group consisting of tetrabutyl ammonium bromide, tetrabutyl ammonium chloride, potassium iodide, sodium iodide, lithium iodide, sodium bromide and potassium bromide.

8. The process according to claim 1, wherein the cyclisation of compound (XI) is carried out in the presence of an inorganic base selected from the group consisting of potassium carbonate, sodium carbonate, potassium bicarbonate, sodium bicarbonate, cesium carbonate, lithium carbonate, sodium hydroxide or potassium hydroxide.

9. The process according to claim 1, wherein the cyclisation is carried out in the presence of a catalyst selected from potassium iodide, sodium iodide, lithium iodide, sodium bromide or potassium bromide.

10. The process according to claim 1, wherein the paliperidone is converted to a pharmaceutically acceptable salt thereof.

* * * * *